United States Patent [19]

Stearns

[11] 4,077,773
[45] Mar. 7, 1978

[54] METHOD AND APPARATUS FOR DETECTION OF MONOALKYLHALIDES

[76] Inventor: Stanley D. Stearns, Box 19032, Houston, Tex. 77024

[21] Appl. No.: 754,539

[22] Filed: Dec. 27, 1976

[51] Int. Cl.$^2$ .................... G01N 27/62; G01N 31/00; G01N 31/06

[52] U.S. Cl. .................... 23/232 R; 23/232 C; 23/232 E; 23/254 R; 23/254 E; 250/302

[58] Field of Search ............ 23/232 R, 232 E, 232 C, 23/254 R, 254 E, 230 M; 250/302, 304

[56] References Cited

U.S. PATENT DOCUMENTS

| | | | |
|---|---|---|---|
| 3,453,081 | 7/1969 | Walker | 23/232 R |
| 3,488,155 | 1/1970 | Ayers | 23/232 R |
| 3,589,171 | 6/1971 | Haley | 23/232 C X |
| 3,711,251 | 1/1973 | Goodson et al. | 23/232 R |
| 3,725,009 | 4/1973 | Lovelock | 23/232 E X |

*Primary Examiner*—Joseph Scovronek
*Attorney, Agent, or Firm*—Donald Gunn

[57] ABSTRACT

A method and apparatus for detection of monoalkylhalides is disclosed. This apparatus contemplates detection of extremely small traces of monoalkylhalides through the nucleophilic substitution of a heavier halogen (preferably iodine) by introducing a sample gas having a monoalkylhalide therein in trace concentrations to be detected and passing it through a closed container providing a surplus of heavier halide ions. An exemplary source of a heavier halide is a container having an alkali iodide therein heated to a temperature sufficiently elevated to initiate iodine disassociation, such as 250° C. An exchange of an iodine for a covalently bound fluorine or chlorine atom is achieved. The monoalkylhalide then has a larger molecular diameter and more complex electronic structure than that originally provided. It also has an enhanced affinity for slow or low energy electrons. This enhances the operation of detection equipment exemplified by an electron capture detector. The sample is passed through a column for separation of other gases and removal of any free iodide and is then passed to a detector. The invention is able to analyze alkenyl halides, however, some halides such as vicinal halides (particularly vinyl chloride) may require hydrogenation prior to transhalogenation.

8 Claims, 2 Drawing Figures

METHOD AND APPARATUS FOR DETECTION OF MONOALKYLHALIDES

BACKGROUND OF THE DISCLOSURE

It has been concluded recently that small traces of many organic halides present serious health problems, including a suspicion that many are carcinogenic agents. The detection of various organic halides in heavy concentrations presents no problem. However, a difficult problem of trace analysis and quantification is a more difficult problem. For example, petrochemical processing plants manufacturing methyl chloride, and vinyl chloride must reduce the volume of these organic halides introduced into the atmosphere for health purposes. It becomes necessary to measure trace quantities of these organic halides in the atmosphere even down to levels such as one part per billion of air, or even smaller concentrations.

It is difficult to provide laboratory equipment which is sensitive to traces of this magnitude and in particular with good specificity relative to that components of interest. The difficulty is more apparent upon departure from the use of laboratory equipment to circumstances where an apparatus must continue to operate at its place of installation indefinitely, for example at a chemical processing plant, in varied outdoor and atmospheric circumstances. It has been discovered that the difficulty in detecting trace chlorides, bromides and trace fluorides, although trace alkyl fluorides are of lesser interest, can be circumvented and yet an accurate and precise quantification thereof can be obtained through the method and apparatus of the present invention. Upon substitution of a heavier and more easily disassociated halogen for a smaller lower cross section more tightly bound halogen in many organic halides, particularly in monoalkylhalides, the sensitivity of detectors can be enhanced substantially. The precise detector utilized is subject to variation, and includes an ionization detector such as an electron capture detector, a photoionization detector, or a spectrophotometric detector. The present process works quite well even with other compounds present in the same sample to provide a quantification of the only specific compound of interest. The response of the detector is measurably enhanced by the substitution through transhalogenation of an iodide ion for a lighter convalently bound chloride or fluoride atom. The response of the electron capture method is enhanced by the replacement of fluorine, chlorine, or bromine by iodine. The increased mass results in easier detection and the formation of a larger signal provides for a more sensitive instrument and method. Also, monoalkyl iodides yield excellent resultants at lower temperatures such as room temperature, while elevated temperatures are required for improved detection of monoalkyl chlorides when using an electron capture detector.

SUMMARY OF THE INVENTION

This invention is directed to a method and apparatus for detection of traces of monoalkylhalides. The invention contemplates nucleophilic substitution of iodine for smaller and more tightly bound chlorine, bromine, and fluorine in monoalkylhalides. The invention contemplates providing apparatus for obtaining a sample of selected volume having a suspected monoalkylhalide therein. A measured sample is introduced into a flowing system and is passed into a transhalogenation reactor. It preferably contains an inorganic compound of iodine, potassium iodide for example. The potassium iodide is heated and provides a surplus of iodide ions for exchange with the lighter halogens in the sample which is introduced. The sample is flowed from the transhalogenation reactor and any remaining free iodine is stripped from the sample. The sample typically will comprise other trace compounds or elements which are separated by passing them through a column. The sample is delivered to a detector, two examples being an electron capture detector or a spectrophotometric detector. The output signal is noted. The output can readily indicate sample levels smaller than one part per billion. If several similar alkyl halides are present, e.g. methyl chloride and methyl bromide, a preliminary separation in a chromatographic column may be very helpful before proceeding with the transhalogenation.

DESCRIPTION OF THE PREFERRED EMBODIMENT

Figure 1:
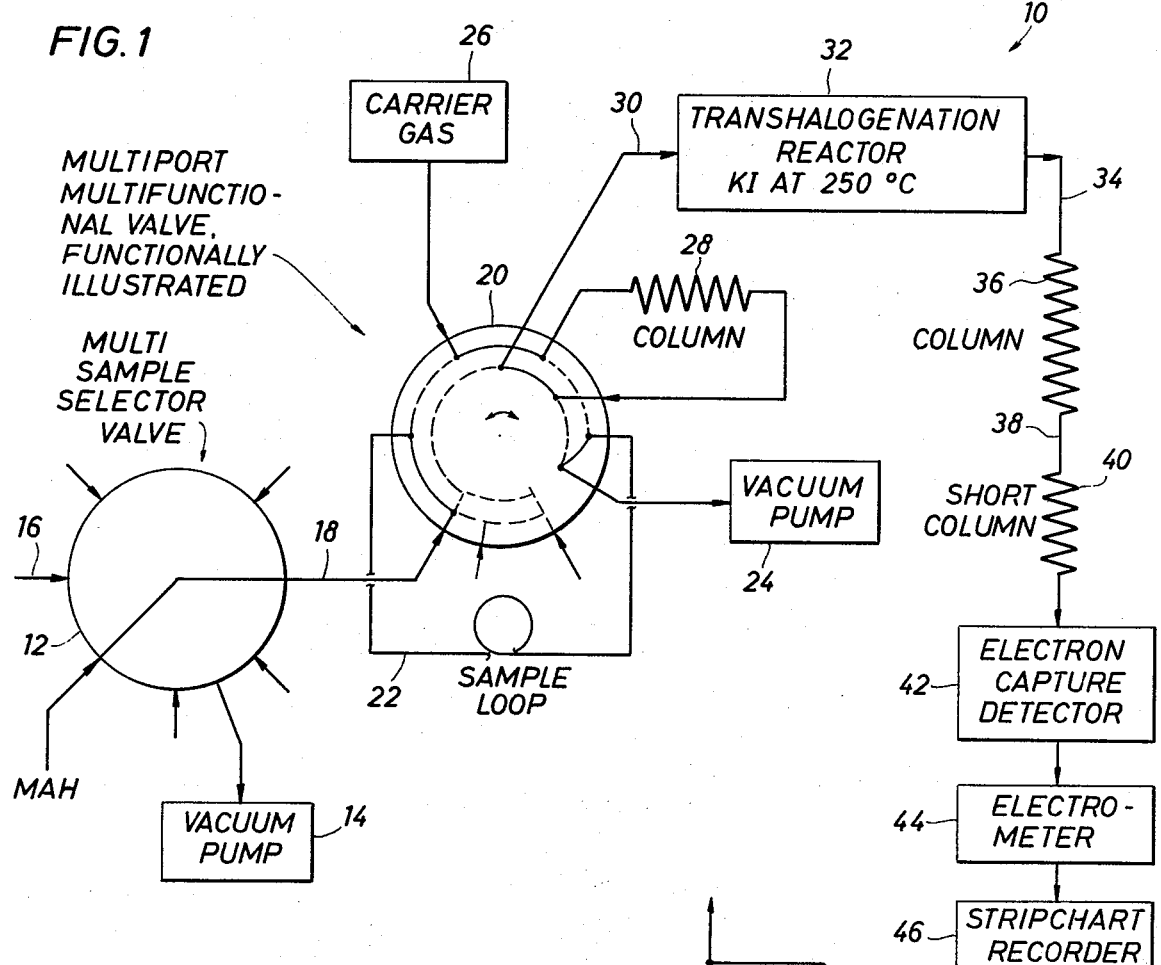
FIG. 1 is a block diagram of a first embodiment of the apparatus of the present invention, the method being disclosed on a description of the specific form of apparatus shown in FIG. 1; and, FIG. 2 is a block diagram schematic of the automatic monitoring apparatus for monoalkylhalides incorporating the techniques of the present invention.

In FIG. 1, an apparatus 10 for detection of minute traces of monoalkylhalides is shown. The apparatus is uniquely able to select and detect minute traces (about one part per billion or less) of organic compounds characterized by a carbon-halogen bond where the halogen is chlorine, bromine or fluorine. The apparatus is able to detect those organic compounds which include a florine, bromine or a chlorine so long as the particular halogen is the only one bound to a particular carbon atom. In FIG. 1, a multi-port, multi-sample selector valve 12 is adapted to be communicated by means of sample lines to a variety of sources of samples. The samples are drawn into the valve by means of a vacuum pump 14. The valve has a rotatable valve element which communicates the pump 12 with a sample source such as that shown at 16. The sample will include a monoalkylhalide of interest. The valve 12 communicates by means of the line 18 to a multi-port, multi-functional valve 20. The valve 20 may have various shapes or forms; it is shown in FIG. 1 defining the flow paths in full line with alternate flow paths in dotted line. The actual construction is not shown. Briefly, the valve has a rotatable element which switches between the two sets of flow paths. Various types of valves are available from commercial sources. The multi-port valve 20 inducts the sample into the valve 20. The valve 20 is a sampling valve. It captures a specified quantity of the sample provided through the line 18. The valve 20 communicates with an additional vacuum pump 24 which provides the flow through the line 18 into the calibrated sample loop 22.

A suitable neutral carrier gas from a source 26 is introduced through the valve element. The valve element is rotated to selectively and periodically communicate a line 30 with the carrier gas and selectively and periodically with the sample provided through the line 18. A filtration column 28 is located in the line 30 to separate any unwanted gasses which might cause an undesired reaction in the downstream apparatus.

The line 30 communicates with a transhalogenation reactor 32. The reactor 32 is preferably filled with an inorganic iodide compound. A typical compound suitable for this purpose is potassium iodide heated to about 250° C at which temperature rapid interchange of ionic iodine to covalently bound halogens occurs. The inorganic material is ground to perhaps sixty or eighty mesh to provide adequate surface area. Alternately, an aqueous iodide solution may be coated onto a passive substrate. The sample is introduced and flowed through the iodide compound in the transhalogenation reactor. The size of the reactor is sufficient to hold a suitable measure of iodine. A larger container is more desirable to reduce the frequency of changes.

The container 32 is a closed vessel. It is filled with finely ground inorganic material, preferably potassium iodide or a coated substrate. It is heated from the exterior to about 250° C. This provides an excess of iodide ions in the container.

A line 34 emerges from the container 32. It communicates with a long separation column 36. The column 36 is packed with a suitable chromatographic packing such as a coated diatomaceous earth to separate fixed gases from the transhalogenated monoalkyliodide flowing into the column. The gas separation occurs during transit through the column 36. To achieve this, the packing is finely ground, typically in the range of eighty to one hundred mesh. The column 36 is maintained at a stabilized temperature, typically 25° C by an external fluid bath or some other means.

The column 36 is connected to an additional line 38. The line 38 conducts the separated gas sample through a column 40. The column 40 need only be a short column. It is typically maintained in a stabilized temperature, preferably room temperature. It provides further separation of the organic iodide of interest.

Some compounds possibly present in the sample injected into the chamber 32 may cause some iodine to flow with the sample. Free iodine is removed by the column 36. The sample then has been stripped of sources of potential detector interference. In this embodiment, an electron capture detector 42 is used. Other types of detectors could be used. The electron capture detector is believed well known in the art. It provides an output to an electrometer 44. The electrometer 44 provides a signal of suitable level to a time variant strip chart recorder 46. The strip chart recorder records the amplitude of the peak of the signal from the detector 42 and its time based correlation with the abscissa yields the concentration of the organic iodide. The organic iodide is the result of a none-for-one exchange for the smaller halide organics previously introduced into the system. The organic iodide is more readily measured in accordance with the teachings of this invention. It enables the electron capture detector to function at greater sensitivities. As a consequence, it enables measurement of traces of organic halides down below one part per billion.

The multi-functional valve 20 is a convenience in operation of the equipment in that it provides timed switching of several functions. It provides timed switching of the carrier gas and the sample, for example. It is possible to substitute multiple valves in the lines as opposed to the single valve 20. However, this increases the cost of manufacture and creates timing problems. The preferable arrangement is the use of a single multi-functional valve such as the valve 20. A suitable commercial source for the multi-functional valve 20 which firm offers a 10 part valve is Valco Instruments Company. The detector 42 is available commercially from Valco Instruments Company. The electrometer 44 is also manufactured by Valco Instruments Company. The strip chart recorder is available from Houston Instruments. Alternate sources can be used.

The method described to this juncture contemplates obtaining a measured sample. The sample is measured by the provision of a gas having a specified volume at controlled pressure and temperature. The volume of gas is selectively introduced into a transhalogenation reactor purged of other gasses except a carrier gas which precedes and follows a sample of interest. The reactor encloses an inorganic compound of iodine, either as a particulate solid or as a coating on an inert solid substrate. It is preferably finely ground to provide adequate surface area. A suitable compound is potassium iodide. The output of the reactor is an altered sample where the halide input thereto have been converted to monoalkyliodides. The sample flowing with other gasses is then separated and those components not of interest are disposed of conveniently by venting to atmosphere. The monoalkyliodide from the sample is then introduced to a detector of some suitable type, an electron capture detector being one suitable device. The appropriate concentration measurement is then made and on comparison with a calibration sample, the measurement of the concentration of the monoalkyhalide is then obtained.

Figure 2:
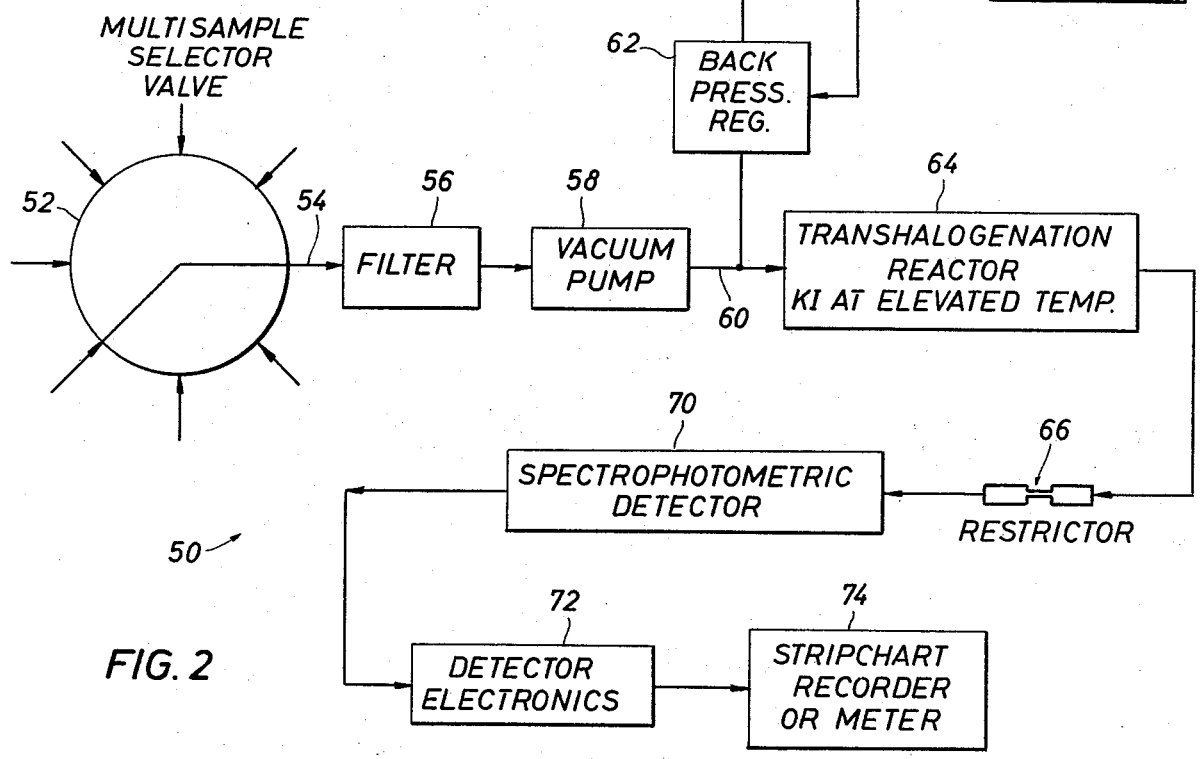

Attention is directed to FIG. 2 which shows an alternative embodiment 50. The test instrument 50 provides continuous monitoring from a single source, or is multiplexed with many sample sources. It incorporates a multi-port, multi-sample selector valve 52. A line 54 is communicated with a filter 56. The valve 52 selects one of several gas sources. It can select only one if desired. It is multiplexed to the several sample sources to provide more versatile operation.

Flow through the line 54 from the sample source is a result of operation of a vacuum pump 58. The vacuum pump 58 provides a flow of the sample gas in a line 60. The line 60 preferably is maintained at a constant pressure level. Variations in pressure which result from switching of the valve 52 or from any other disturbance are accommodated by a back pressure regulator 62. This introduces the sample of interest into a transhalogenation reactor 64. The description of the reactor 32 given above will suffice for the reactor in this embodiment. The flow of gasses from the reactor 64, including the organic halide of interest, is then delivered to the restrictive filter 66. The restrictor 66 functions in the same manner as the previously described column 36 in the first embodiment. It strips excess iodine from the gas flow and separates the sample gas of interest from other gasses in the sample. Its operation results in delivery of separated gasses to a spectrophotometric detector 70. The detector 70 provides an output signal to suitable detector electronics 72 representative of the concentration of the gas of interest in the sample. A signal is formed for a strip chart recorder or other suitable instrument 74. A simple meter movement can be used. Since permanent records are normally desirable, a recording instrument of some sort is used and a strip chart recorder utilizing a clock drive for the abscissa is normally preferred.

The detector 70 responds to the substituted monoalkyliodide. It provides an output measure which, in comparison with the calibration standard, represents the concentration of the monoalkylhalide input to the test apparatus 50. As a preliminary step, it is helpful in some instances to hydrogenate a vicinal halide prior to the step of introducing the vicinal halide sample into the transhalogenation reactor.

Many alterations and variations in the method and apparatus disclosed can be incorporated without departing from the scope of the present invention. The scope is determined by the claims which follow.

I claim:

1. A method of detecting traces of a monoalkylhalide comprising the steps of introducing a measured sample of gas of interest into a transhalogenation reactor having a surplus of iodine as an iodide therein for exchange therewith to form a monoalkyliodide and thereafter using a detector means to obtain a measure of the concentration thereof.

2. The method of claim 1 wherein the transhalogenation reactor has a surplus of available iodine for substitution and any free iodine flowing with the sample to the detector means is removed therefrom.

3. The method of claim 1 wherein an inorganic iodide is heated to an elevated temperature to enable stoichiometric transhalogenation.

4. The method of claim 1 wherein other gasses not of interest are removed from the sample prior to the step of using the detector means to measure the concentration thereof.

5. The method of claim 1 wherein the sample is measured at a standardized pressure, volume and temperature.

6. The method of claim 1 including the step of first hydrogenating a vicinal halide prior to the step of introducing the sample into the transhalogenation reactor.

7. The method of claim 1 including the step of heating potassium iodide to about 250° C and thereafter substituting the halogen in the monoalkylhalide with iodine from the potassium iodide.

8. The method of claim 1, including the step of heating potassium iodide to about 250° C. to enable stoichiometric transhalogenation and thereafter measuring the iodide exchanged sample after removing surplus free iodine.

* * * * *